United States Patent [19]

Stoy et al.

[11] Patent Number: 5,736,127
[45] Date of Patent: Apr. 7, 1998

[54] POLYMERIC NITROGEN-CONTAINING DRUG SALT FORMS FOR CONTROLLED RELEASE

[75] Inventors: Vladimir A. Stoy; Charles K. Kliment, both of Princeton, N.J.

[73] Assignee: Hymedix International, Inc., Dayton, N.J.

[21] Appl. No.: 711,345

[22] Filed: Sep. 5, 1996

Related U.S. Application Data

[63] Continuation of Ser. No. 201,357, Feb. 24, 1994, abandoned, which is a continuation-in-part of Ser. No. 864,050, Apr. 6, 1992, abandoned.

[51] Int. Cl.$^6$ .................................................. A61K 31/74
[52] U.S. Cl. ........................... 424/78.02; 424/78.04; 424/78.17; 424/78.35; 514/772.6
[58] Field of Search .................. 424/78.02, 78.04, 424/78.17, 78.35; 514/772.6

[56] References Cited

U.S. PATENT DOCUMENTS

| | | | |
|---|---|---|---|
| 4,221,778 | 9/1980 | Raghunathan | 424/483 |
| 4,943,618 | 7/1990 | Stoy et al. | 525/340 |
| 4,997,643 | 3/1991 | Partrain, III et al. | 424/78 |

OTHER PUBLICATIONS

Chemical Abstracts 111:12365, "New Type of Hydrogel for Controlled Drug Delivery", Vladimir A. Stoy, 1989.

*Primary Examiner*—Frederick Krass
*Attorney, Agent, or Firm*—Kenneth P. Glynn, Esq.

[57] ABSTRACT

The present invention is directed to a composition comprising a nitrogen-containig drug-polymer salt and a method for making said composition. The drug-polymer salt is comprised of one or more drugs having basic groups as part of their chemical structure which are capable of forming salts with acids and one or more hydrophilic polymers containing carboxylate groups and amidine groups as pendant groups. Such polymeric salts of drugs have been found to have excellent bio-availability and advantageous release profiles in various forms (gels, ointments, pills, etc.). Particularly advantageous polymers contain pendant nitrile groups in addition to carboxyls and amidines which provide the polymer with hydrogel characteristics.

12 Claims, 2 Drawing Sheets

POLYMERIC NITROGEN-CONTAINING DRUG SALT FORMS FOR CONTROLLED RELEASE

REFERENCE TO RELATED APPLICATIONS

This application is a continuation of application Ser. No. 08/201,357 filed Feb. 24, 1994, now abandoned, which is a continuation-in-part of U.S. patent application Ser. No. 07/864,050 filed on Apr. 6, 1992 and now abandoned, entitled "Novel Drug Forms with Controlled Release Capabilities" by the inventors herewith.

BACKGROUND OF THE INVENTION

1. Field of the Invention

The present invention is directed to a composition comprising nitrogen-containing drug-polymer salts and method for making the compositions. These drug-polymer salts provide advantageous release profiles and provide excellent bio-availability in various forms such as gels, ointments and tablets.

2. Prior Art Statement

An important characteristic of various bioactive substances (pharmaceuticals, OTC medicines, biocides, repellents, etc., hereinafter collectively referred to as "drugs" or "drug") is their "bio-availability" or active concentration in a form which can be absorbed and utilized by a target organism or organ. In many cases, the bio-availability is related to the drug solubility in water.

The drug should be available in the soluble form in a proper concentration range for a required period of time. To achieve these and other properties, drugs are used in various drug forms (e.g. pills, capsules, solutions, ointments etc.) Particularly advantageous are drug forms which provide a constant rate of drug release (so called "zero-order release"). The systems providing this release profile are often complicated and expensive.

One of the drug forms is drugs incorporated in polymer matrices. Drugs containing ionogenic groups are sometimes combined with ion-exchange resins to form mutual salts. The incorporation of the drug into the solid polymer matrix can increase its stability, mask its taste or odor, modify its bio-availability and so on (see e.g. Y. Raguhunathan: U.S. Pat. No. 4,221,778).

The drugs containing cationic groups (such as amino-groups, amidine groups, imino-groups etc.) are bound to cation-exchange resins containing functional anionic groups, such as carboxyls, sulfo-groups, sulphate groups and so on.

There are numerous drugs containing cationic groups, such as the following:

TETRACYCLINE:

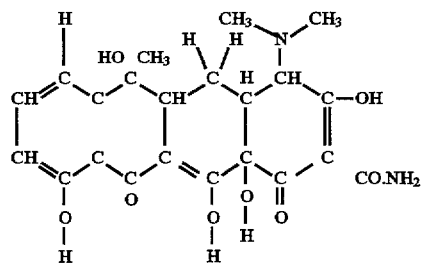

LIDOCAINE:

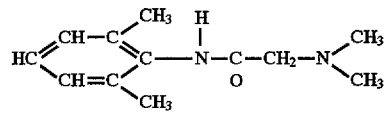

PILOCARPINE:

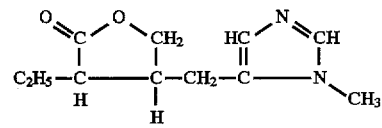

Other suitable drug examples are phenylisopropylamine (Amphetamine), Amrinone, Pitpamperone, Pipemidic Acid, Piperazine, Oxolamine, Oxethazain, Oxeladine, Ocymethazoline, Chlorpheniramine, Loperamide, Procaine, Acetophenazine, Aminopromazine, Aminopyrine and others.

Very often such drugs are poorly soluble in water in their free base form. Their salts with organic or inorganic low molecular acids are typically more soluble than the respective free bases.

Drugs forming salts with insoluble ion-exchange resins are not available in the solution unless exchanged for a cation (such as Na+). The drug thus has limited availability in the solution as corresponds to the respective equilibrium, for example:

The concentration of the drug available in the soluble form (here as hydrochloride) is controlled by the availability of an appropriate counter-cation. In its absence (e.g. if the ion-exchange resin with the incorporated drug is dispersed in pure water) the drug is essentially insoluble (its concentration in the solution is controlled by the concentration of $H_3O^+$ which is low in pure water and in neutral or alkaline media).

This type of drug immobilization can extend the time of drug release, but does not meet the requirement of constant rate of drug release: the equilibrium concentration of the drug in solution is proportional to the residual concentration of the drug in the salt form, which decreases with time. The release profile is thus exponential with respect to time, as it is with most systems relying on plain dissolution.

Another limitation of this approach is that the capacity of the carrier is limited by concentration of the immobilized ionic groups.

SUMMARY OF THE INVENTION

The present invention is directed to a composition comprising a nitrogen-containing drug-polymer salt and a method for making said composition. The drug-polymer salt is comprised of one or more drugs having basic groups as part of their chemical structure which are capable of forming salts with acids and one or more hydrophilic polymers containing carboxylate groups and amidine groups as pendant groups. Such polymeric salts of drugs have been found to have excellent bio-availability and advantageous release profiles in various forms (gels, ointments, pills, etc.). Particularly advantageous polymers contain pendant nitrile groups in addition to carboxyls and amidines which provide the polymer with hydrogel characteristics.

DETAILED DESCRIPTION OF THE PRESENT INVENTION

Figure 1:
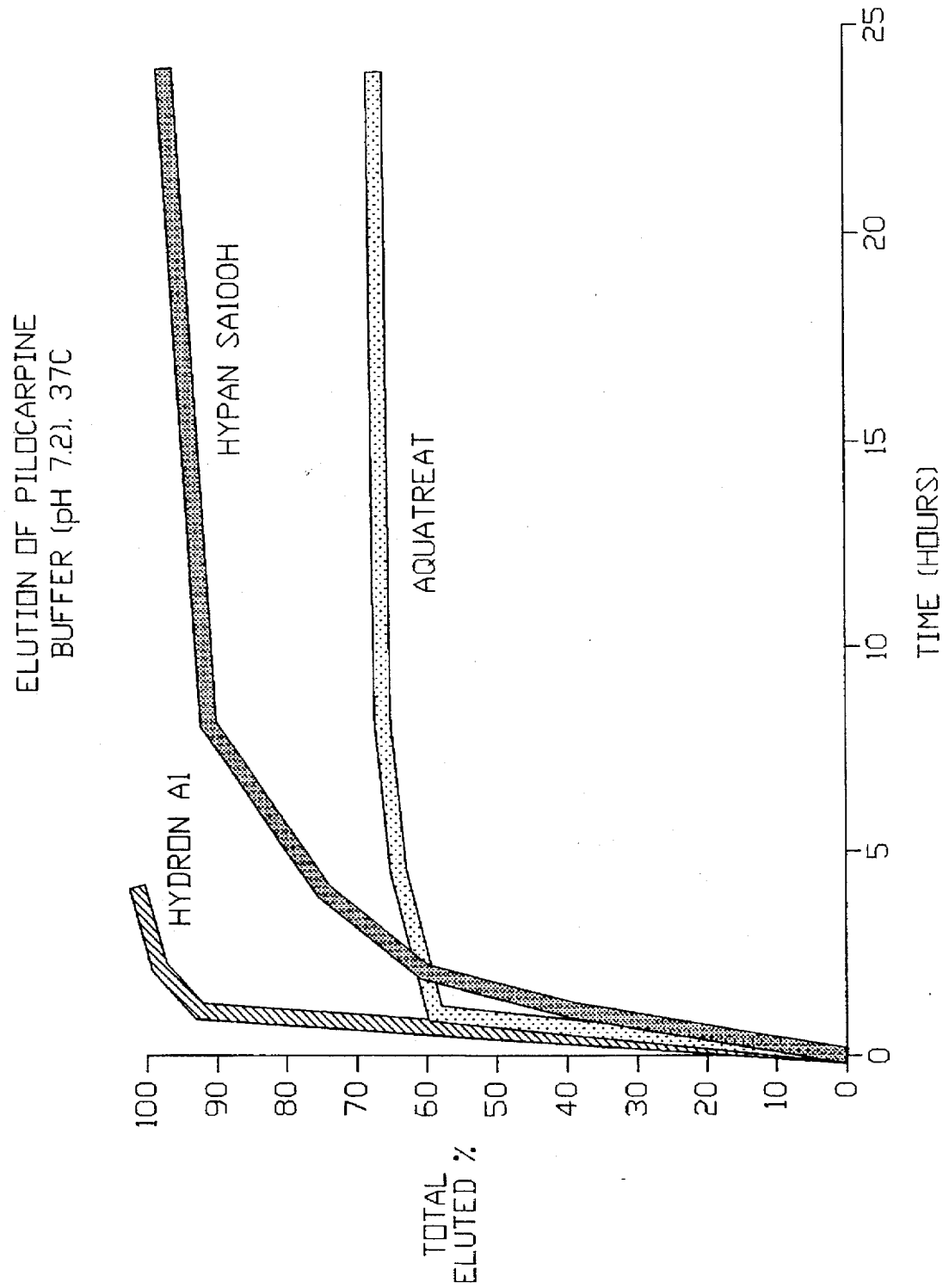
FIGS. 1 and 2 show the elution profiles of pilocarpine and tetracycline, respectively, from various polymer drug salts which are discussed in detail in the working examples.
Figure 2:
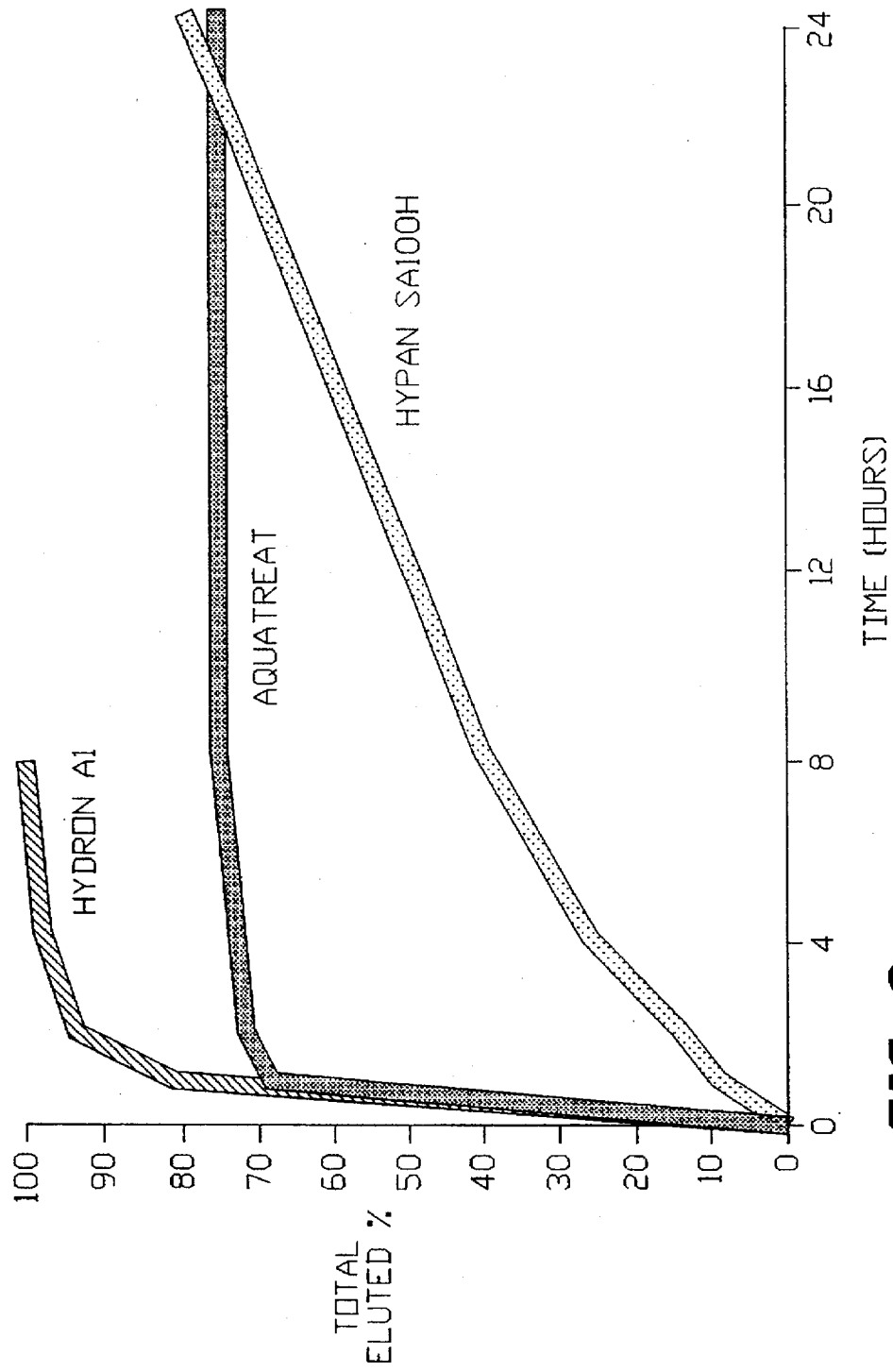

We have now found that formulations comprising:

1) drugs with basic groups (primary, secondary and tertiary amines, imines, amidines, and other nitrogen-containing groups capable of forming salts with acids [such as hydrochlorides]), and
2) hydrophilic polymers containing carboxyls and amidines as pendant groups, form hydrophilic salts with improved and controlled bioavailability of the drug, often with zero-order release characteristics.

Particularly advantageous are polymers containing pendant nitrile groups (in addition to said carboxyls and amidines) which provide the polymer with hydrogel character (i.e. limited swelling and substantial insolubility in water).

Polymers of said composition are, for instance, products of alkaline hydrolysis of polyacrylonitrile according to U.S. Pat. No. 4,943,618.

Said polymeric salts of drugs have excellent bio-availability and advantageous release profiles in various forms (gels, ointments, pills etc). Contrary to other polymeric salts, the drugs are released at a constant rate over time as shown in the Examples.

The reasons for this difference are not known at present. These experimental observations cannot be readily explained on a theoretical basis. There are indications that the observed high efficacy is somehow related to the ability of the polymer chain to form internal salts around its isoelectric point.

Polymers with carboxylate and amidine groups on the same chain have an amphoteric character. These groups form a mutual internal salt at certain pH values (typically between pH 3 and 4) with minimum swelling in water.

For instance, polymers containing carboxyl-amidine-carboxyl triads form internal salts at pH 3.6 to 3.8:

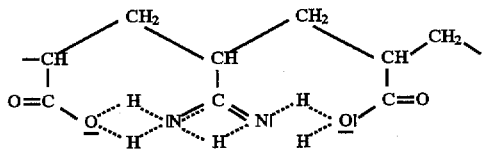

The triad in this arrangement is substantially hydrophobic and polymers containing such groups will have limited swelling at such pH.

This sequence is capable of reacting with organic bases, such as various drugs in the free-base form, to form a polymeric salt of the given drug. At the same time, the internal salt in the polymer is broken and the polymer becomes more hydrophilic.

In the case when the drug is insoluble in its free-base form, the drug and the polymer hydrophilize (or even solubilize) each other.

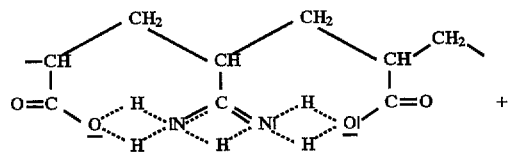

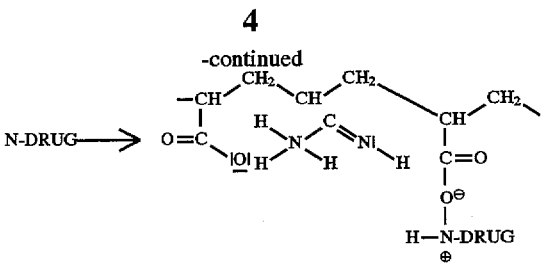

The drug-polymer salt effectively immobilizes the drug. It is released by ionic exchange in its water-soluble salt form:

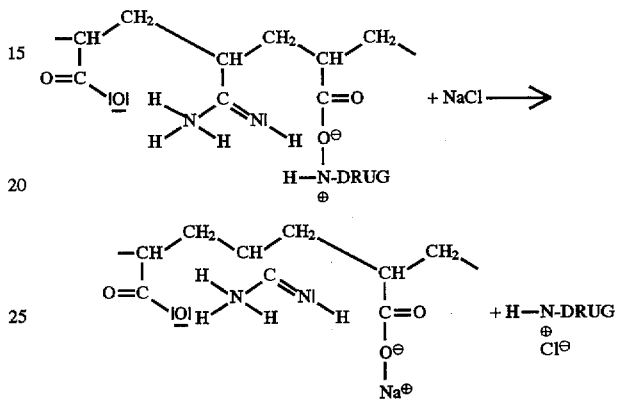

Another possible mechanism contributing to the improved bioavailability and release profile is the formation of emulsions, multiple emulsions, and micro-emulsions. Hydrophilic polymers which also contain nitrile pendant groups (and nitrile groups in continuous sequences or blocks in particular) are effective emulsifiers as described in U.S. application Ser. No. 07/043,327 filed by Vladimir A. Stoy and Jan Lovy on Apr. 28, 1987, assigned to Kingston Technologies, Inc., now abandoned and incorporated by reference herein. Such polymers can solubilize the free-base drug in the aqueous phase by forming a micro-emulsion and contribute thus to the bioavailability and to the time-release profile of the drug. The formation of microemulsions (or other such solubilization mechanism) could explain the fact that the amount of a drug solubilized by the polymer is often much greater than would correspond to the concentration of immobilized binding groups.

Copolymers containing sufficient concentrations of nitrile groups form strong, rubbery hydrogels. The hydrogels comprising combinations of hydrophilic groups as described can be used to absorb the drug and thus form a reservoir for long-term drug release.

The drug-releasing hydrogels of the present invention can be made in various forms and have different functions: membrane or film, tubing or catheter, insert or implant, capsule etc. The drug-releasing hydrogel composition may take the form of a dry substance such as a pill or tablet. The composition may be an emulsion, a viscous aqueous solution or a spreadable aqueous gels, any of which may be used, for example, as a topical or injectable formulation or an ophthalmic formulation containing, for example, the drug pilocarpine. The drug-polymer salt composition may also be an elastic hydrogel which may take the form of a hydrogel dispersion in a liquid, a coating, a pill, an implantable device or an insertable device such as part of a catheter. The drug chosen for the drug-polymer salt may be anesthetic, antibiotic, antihistamine, cytostatic, etc.

The drug-polymer salts can be made in various ways. One preferred method consists of neutralizing the drug by the internal polymer salt (or vice versa) in the presence of water. After the neutralization the water may optionally be fully or partly evaporated, depending on the desired consistency (gel, solution, slurry, powder, coating etc.) Once desired consistency is obtained, a skin lubricant such as mineral oil may optionally be added and the mixture heated and homogenized to form an emulsion for applying to the skin.

An alternative method consists of mixing the dry powders of both components and compressing the mixture to form a tablet. Alternatively, a skin lubricant such as mineral oil may be added to the dry powder and the mixture heated and homogenized to form an emulsion for applying to the skin.

EXAMPLES

Two multiblock hydrophilic HYPAN™ polymers (Kingston Technologies, Inc., Dayton, N.J.) described in U.S. Pat. No. 4,943,618 and incorporated herein were used, designated SA100H and SA200H. They were prepared by heterogeneous alkaline hydrolysis, as described in U.S. Pat. No. 4,943,618, by coagulating a solution of polyacrylonitrile in water to form an "aquagel", and reacting this aquagel with a solution of sodium hydroxide in water.

This hydrolysis converts part of the nitrile groups to amidines, amides and carboxy groups. Two polyacrylonitrile aquagel polymers were hydrolyzed and differ by the degree of hydrolysis:

| POLYMER | NITRILE GROUPS | AMIDINES | AMIDES | CARBOXY GROUPS |
|---------|----------------|----------|--------|----------------|
| SA100H  | 24.0%          | 15.2%    | 9.9%   | 50.9%          |
| SA200H  | 16.0%          | 16.8%    | 10.9%  | 56.3%          |

The composition of the hydrophilic blocks of these polymers is such that an amidine group is flanked by two carboxy groups. At the isoelectric point, these three groups form an internal salt, and thus at pH of 3.6–3.8, these polymers are basically hydrophobic and do not swell in water. Once they are neutralized with a suitable base (this base in this instance being a drug), the internal salt "opens" and the polymers swell strongly in water, forming gels.

HYPAN SS201 is basically the SA200H grade, which has been neutralized with ammonium carbonate.

EXAMPLE 1

Polymer used: SA100H
Drug used: LIDOCAINE
2(Diethylmino)-N-(2,6-dimethyl-phenyl)acetamide
Sample Preparation (All Parts by Weight)

9.4 parts of the polymer were mixed in 86.5 parts of water to form a suspension. When all the polymer was thoroughly wetted, 14.7 parts of Lidocaine were mixed in thoroughly. Gel started forming after about 20 seconds. In about one minute, strong, dense gel was formed. This gel contained 13.3% of Lidocaine.

Part of the gel was placed into a bag, prepared by heat-sealing non-woven polypropylene. The bag was placed into 300 cc of phosphate buffer (pH 6.9) in a mixing container, which was kept at 37° C. Samples were taken at various intervals and were evaluated By UV spectrophotometry, reading the absorption at 261 nm and evaluating it using a calibration curve, constructed by using solutions of known Lidocaine concentration.
Results The total loading of 450 mg was eluted in ten hours at a steady (zero-order) release rate of 45 mg/hour.

EXAMPLE 2

Polymer used: SA200H
Drug used: LIDOCAINE
Sample Preparation

As in Example 1, only 8.6 parts of polymer, 14.8 part of drug and 76.5 parts of water were used for 14.8% loading. Elution was performed as in Example 1.
Results The total loading of 530 mg was eluted in 12 hours at a steady (zero-order) rate of 44 mg/hour.

EXAMPLE 3

Polymer used: SA100H
Drug used: LIDOCAINE
Sample Preparation

As in Example 1, but for a low loading of drug, 3.1 parts of polymer, 0.6 parts of drug and 99.9 parts of water were used for Lidocaine loading of 0.6%. The gel was much less dense than in Example 1. Elution was done as in Example 1.
Results The total loading of 48 mg eluted in 12 hours at a steady rate (zero-order) of 4 mg/hour.

EXAMPLE 4

Polymer used: SA200H
Drug used: LIDOCAINE
Sample Preparation

As in Example 1, 3.1 parts of polymer, 0.6 parts of the drug and 105.9 parts of water were used for a Lidocaine loading of 0.6%. The loose gel passed easily through an 18 gauge needle and once the shear was removed, reconstituted to a non-flowing configuration. Elution was done as in Example 1.
Results The total loading of 66 mg was eluted in 14 hours at a steady rate (zero-order) of 4.7 mg/hour.

EXAMPLE 5

Polymer used: SA100H
Drug used: LIDOCAINE
Sample Preparation

A gel was prepared according to Example 1 from 2.5 parts of polymer, 4.3 parts of the drug and 600.0 parts of water. Into this gel, 400.0 parts of light mineral oil was mixed and an emulsion was prepared by heating the mixture to 40°–45° C. and homogenizing it on a high-speed homogenizer.

The resulting smooth, viscous emulsion can be spread easily on skin, where it forms a continuous layer of the polymer, containing the drug. This layer keeps the drug in situ and active for at least eight hours, as tested by pricking the covered spot repeatedly with a needle and monitoring the anaesthetizing effect of the drug.

EXAMPLE 6

Polymer used: SA100H
Drug used: TETRACYCLINE 4-(dimethylamino)-1,4,4a,5,5a,6,11,12a-octahydro-
3,6,10,12a-pentahydroxy-6-methyl-1,11-dioxo-2-
naphtacenecarboxamide
Sample Preparation 9.4 parts of the polymer were mixed in 85.4 parts of water until thoroughly wetted. 15.0 parts of Tetracycline were added and thoroughly mixed. The dry polymer complex was substantially insoluble, forming a low viscosity slurry. To increase the viscosity, a small amount of base was added to increase the pH. Finally, 2 parts of ammonium carbonate were added. Gel formed in about 30 seconds.

The elution was performed as described in Example 1, UV absorbance was read at 273 nm and was evaluated using a calibration curve.

Results 200 mg of total loading were eluted in 32 hours at a steady (zero-order) rate of 6.3 mg/hour.

EXAMPLE 7

Polymer used: SA200H

Drug used: TETRACYCLINE

Sample Preparation 5 parts of the polymer were mixed with 85 parts of water and thoroughly wetted. 5 parts of Tetracycline were added and mixed in. Since tetracycline is substantially hydrophobic even in its salt form, the tetracycline-polymer mixture formed a low viscosity slurry. A weak base (5 parts of triethanolamine) was added to achieve gel consistency.

Dense gel formed in about 30 seconds. The gel was eluted as in Example 1 and UV absorbance was evaluated using the calibration curve.

Results 110 mg of total loading were eluted at a zero-order rate of 0.8 mg/hour in 156 hours total time.

EXAMPLE 8

Polymer used: SS201

Drug used: TETRACYCLINE

Sample preparation

A mixture of 3 parts of the drug and 7 parts of dry, finely powdered polymer was prepared by tumbling the two powders together in a roller mill for 10 minutes. One gram of the mixture was filled into an open plastic mold, which was kept at 100% relative humidity for 12 hours.

The powder in the molds was compressed in a Carver press at 2,000 psi pressure, and the resulting tablet was dried in a hot-air oven at 70° C. for one hour. After removal from the molds, the tablets were sealed in non-woven polypropylene bags. Some were eluted in phosphate buffer (pH 6.9) and some were eluted in saline (pH 6.7), both elutions for 56 hours at 37° C. in mixing containers. Samples were taken at regular intervals and were evaluated by UV spectrophotometry, reading absorbance at 273 nm and by reading concentrations from a calibration curve.

Results

Both elutions were basically of the zero-order. The elution in saline showed an elution rate of 0.8 mg/hour, while the elution rate in the buffer was double that, 1.6 mg/hour. The amount of drug eluted was only about 20–30% of the original loading.

EXAMPLE 9

Polymer used: SA200H

Drug used: PILOCARPINE 3-ethyldihydro-4-[(1-methyl-1H-imidazol-5-yl) methyl]-2(-3H)-furanone Sample Preparation 1.25 parts of the polymer were mixed into 96.75 parts of water and thoroughly wetted. 2 parts of the drug were added and mixed until a loose gel formed (in about 60 seconds). The gel was used in animal trials on monkeys.

The gel was instilled under the lower eyelid and left in situ for six hours. The effect of the drug was monitored by the dilation of the pupil of the tested eye. The preparation was compared with a commercial Pilocarpine carrier in the same concentration.

Results

The pupil of the eye with the Pilocarpine-gel formulation remained dilated over 55% after the six-hour period. Extrapolation beyond six hours showed no decrease in the dilation indicating much longer effect than the six hours monitored in this experiment. The control eye pupil's dilation was less than 35% after two hours and less than 15% after six hours. This comparison shows clearly the prolonged effect of the drug in vitro when using the HYPAN™ gel.

EXAMPLE 10

Polymer used: SA100H

Drug used: CYTOSINE 4-amino-2-oxo-1,2-dihydropyrimidine

Sample Preparation

The drug containing gel was prepared as in Example 7 from 10 parts of the polymer, 8 parts of Cytosine, 6 parts of triethanolamine and 76 parts of water. The elution was performed as in Example 1 and the concentration was read at 267 nm. The dense gel can still be injected through a 12–14 gauge needle and deposited in the vicinity of a tumor to provide a localized controlled release of the drug.

Results

In vitro elution rate was found to be zero-order. The total loading of 800 mg was eluted during 48 hours at a rate of 16 mg/hour.

EXAMPLES 11–16

A series of concurrent tests were conducted in order to determine, evaluate and compare the release of drugs from polymers containing carboxy groups which are known in the prior art and the release of the same drugs from "HYPAN™" (Kingston Technologies, L.P., Dayton, N.J.) polymers taught in the present invention.

Three polymers were used. They are as follows:

HYDRON A1: (made by Hydron Laboratories, Inc., New Brunswick, N.J.) is a copolymer of 90% hydroxyethylmethacrylate and 10% of methacrylic acid, MW approx. 120,000 Daltons, non-crosslinked.

AQUATREAT AR-7-H: (made by Alco Chemical, Chattanooga, Tenn.) is a 15% solution of polyacrylic acid in water, MW approx. 1,000,000 Daltons.

HYPAN SA100H: (made by Kingston Technologies, Inc. Dayton, N.J.) is a multiblock copolymer of acrylonitrile and hydrophilic blocks containing carboxyl-amidine-carboxyl triads, MW 150,000 Daltons.

Two drugs were used. They are as follows:

PILOCARPINE: 3-ethyldihydro-4[(1-methyl-1H-imidazole-5-yl)methyl]-2(-3H)furanone TETRACYCLINE: 4-(dimethylamino)-1,4,4A,5,5A,6, 11,12a-octahydro-3,6,10,12a-pentahydroxy-6-methyl-1,11-dioxo-2-naphthacenecarboxamide Thus, Examples 11, 12 and 13 respectively relate to the use of the three above mentioned polymers with Pilocarpine, respectively, and Examples 14, 15 and 16 to the use of these polymers with Tetracycline, respectively.

Preparation of samples was as follows:

HYDRON A1: The polymer was dissolved as 20% solids in ethyl-alcohol (95%) and the drug was added in a molar ratio assuring 100% neutralization of the carboxy groups of the methacrylic acid.

The drug-polymer salt was retrieved in a dry form by evaporating the alcohol at 60° C. overnight.

AQUATREAT AR-7-H: The acid was neutralized in its 15% water solution with the drug to such an extent that the concentration of the drug in the sample was kept between 250 and 300 mg.

The remaining free carboxyls were fully neutralized by a proper amount of calcium hydroxide. A tough gel resulted.

HYPAN SA100H: The powdery polymer was dispersed in distilled water and an amount of the drug sufficient for a full neutralization of its carboxy groups was added. A solid gel resulted in about 60 seconds. The sample size was deliberately chosen so that its drug loading will be between 250–300 mg.

MEASUREMENTS

For both drugs, UV calibration curves were constructed, using solutions of known concentrations of each drug.

The samples were weighed on an analytical into prepared "tea bags" made from non-woven polypropylene and heat sealed. HYDRON A1 in dry form, the other two as wet gels.

All elutions were conducted at 37° C. in 300 g of a phosphate buffer (pH 7.2) in a mixed container. 3 cc samples were withdrawn after 1, 2, 4, 8, and 24 hours. After taking each sample, 3 cc of fresh buffer solution was added back to the main container to maintain its weight at 300 g.

The samples were diluted gravimetrically with the phosphate buffer ratios approximately between 1:6–1:10, as their drug concentrations were generally too high for direct reading. The diluted samples were measured on a UV Spectrophotometer at 215 nm (Pilocarpine) and 273 nm (Tetracycline). Concentration obtained from the calibration curves were multiplied by 300 (size of sample) and the proper dilution to obtain the drug's concentration in the 300 g sample. Comparing the drug's concentration at each time to the original known loading of the drug in the sample, percent of the drug eluted at each time was obtained.

Results

| | PILOCARPINE ELUTIONS | | | | | |
|---|---|---|---|---|---|---|
| TIME | EXAMPLE 11 HYDRON A1 load 233 mg | | EXAMPLE 12 AQUATREAT VR-7-H load 734 mg | | EXAMPLE 13 HYPAN SA100H load 211 mg | |
| (hrs) | mg | % | mg | % | mg | % |
| 1 | 213 | 91.4 | 430 | 58.6 | 77 | 36.4 |
| 2 | 226 | 97.0 | | | 127 | 60.2 |
| 4 | 236 | 100.0 | 464 | 63.2 | 157 | 74.4 |
| 8 | | | 481 | 65.6 | 190 | 90.0 |
| 24 | | | 490 | 66.7 | 202 | 96.0 |

| | TETRACYLINE ELUTIONS | | | | | |
|---|---|---|---|---|---|---|
| TIME | EXAMPLE 14 HYDRON A1 load 270 mg | | EXAMPLE 15 AQUATREAT VR-7-H load 255 mg | | EXAMPLE 16 HYPAN SA100H load 291 mg | |
| (hrs) | mg | % | mg | % | mg | % |
| 1 | 220 | 81.4 | 175 | 68.6 | 25 | 8.6 |
| 2 | 254 | 94.0 | 184 | 72.1 | 32 | 11.1 |
| 4 | 265 | 98.0 | 187 | 73.2 | 74 | 25.3 |
| 8 | 272 | 100.0 | 193 | 75.6 | 116 | 40.0 |
| 24 | | | 196 | 76.7 | 233 | 80.1 |

From these results it is clear that drug release from salts of the drugs and polymers containing carboxyl groups does not give either prolonged release or zero order release.

Present invention compositions using HYPAN™ polymers with their carboxy-amidine-carboxyl triads show both prolonged (24 hours for Pilocarpine, over 30 hours for Tetracycline) release and near to zero order release as well.

Obviously, numerous modifications and in light of the above teachings. It is therefore understood that within the scope of the appended claims the invention may be practiced otherwise than as specifically described herein.

What is claimed is:

1. A composition, comprising:

a drug-polymer salt comprising a therapeutically effective amount of a nitrogen-containing drug, and comprising at least the following constituents:
(a) a drug a having basic nitrogen group as part of its chemical structure, said basic group being capable of forming a salt with an acid; and,
at least one hydrophilic polymer containing pendant carboxyl-amidine-carboxyl triads.

2. The composition of claim 1 wherein at least one of said hydrophilic polymers is a hydrolyzed polyacrylonitrile containing said triads.

3. The composition of claim 1 wherein said nitrogen containing drug is a drug selected from the group consisting of an anesthetic, antibiotic, antihistamine and cytostatic.

4. The composition of claim 1 wherein said composition is an emulsion containing additional dispersed water-insoluble components.

5. The composition of claim 4 wherein said emulsion is an ophthalmic formulation.

6. The composition of claim 4 wherein said drug is pilocarpine.

7. The composition of claim 1 wherein said composition is a viscous aqueous solution containing greater than 95% water.

8. The composition of claim 7 wherein said viscous aqueous solution is an ophthalmic formulation.

9. The composition of claim 8 wherein said drug is pilocarpine.

10. The composition of claim 1 wherein said composition is a spreadable aqueous gel containing greater than 95% water.

11. The composition of claim 10 wherein said spreadable aqueous gel is an ophthalmic solution.

12. The composition of claim 11 wherein said drug is pilocarpine.

* * * * *